(12) United States Patent  
Kraft

(10) Patent No.: US 8,409,147 B2  
(45) Date of Patent: Apr. 2, 2013

(54) RAPID LOCAL ANESTHESIA LINEAR INJECTION DEVICE

(76) Inventor: Joseph Wayne Kraft, College Station, TX (US)

( * ) Notice: Subject to any disclaimer, the term of this patent is extended or adjusted under 35 U.S.C. 154(b) by 58 days.

(21) Appl. No.: 13/026,167

(22) Filed: Feb. 11, 2011

(65) Prior Publication Data

US 2011/0137250 A1    Jun. 9, 2011

Related U.S. Application Data

(63) Continuation-in-part of application No. 12/545,829, filed on Aug. 22, 2009, now Pat. No. 8,088,108.

(51) Int. Cl.  
*A61M 5/00* (2006.01)

(52) U.S. Cl. ........................................................ 604/173

(58) Field of Classification Search .................. 604/116, 604/173, 187, 272–274, 310, 311  
See application file for complete search history.

(56) References Cited

U.S. PATENT DOCUMENTS

| | | | | |
|---|---|---|---|---|
| 665,608 | A * | 1/1901 | Kotz | 132/115 |
| 2,696,212 | A * | 12/1954 | Dunmire | 604/195 |
| 3,595,231 | A | 7/1971 | Pistor | |
| 3,941,126 | A | 3/1976 | Dietrich | |
| 4,150,669 | A * | 4/1979 | Latorre | 604/191 |
| 4,586,490 | A | 5/1986 | Karz | |
| 6,518,255 | B2 | 2/2003 | Rosengart | |
| 6,537,242 | B1 | 3/2003 | Palmer | |
| 6,623,457 | B1 | 9/2003 | Rosenburg | |
| 6,743,211 | B1 | 6/2004 | Prausnitz | |
| 6,960,193 | B2 | 11/2005 | Rosenburg | |
| 7,047,070 | B2 | 5/2006 | Wilkinson | |
| 7,131,960 | B2 | 11/2006 | Trautman | |
| 7,479,134 | B2 | 1/2009 | Olejnik | |
| 2004/0186419 | A1 | 9/2004 | Cho | |
| 2006/0259006 | A1 * | 11/2006 | McKay et al. | 604/506 |
| 2007/0270757 | A1 | 11/2007 | Willis | |
| 2008/0208208 | A1 | 8/2008 | Tomono | |
| 2009/0043250 | A1 | 2/2009 | Gonnelli | |
| 2009/0054842 | A1 | 2/2009 | Yeshurun | |
| 2010/0256594 | A1 * | 10/2010 | Kimmell et al. | 604/506 |

* cited by examiner

*Primary Examiner* — Kevin C Sirmons  
*Assistant Examiner* — Kami A Bosworth  
(74) *Attorney, Agent, or Firm* — Furr Law Firm; Jeffrey Furr, Esq.

(57) ABSTRACT

This is a Rapid Local Anesthesia Linear Injection Device. It is made of a very simple triangular shaped piece of clear plastic with encased conduits connecting a flange on the tip of the cone where a Luer lock syringe can attach, and the base where there are a multiple tiny hypodermic needles protruding from the base of the triangle. The number of needles would be directly proportional to the length of the base of the device. It would be available in many sizes identified by the shape and the length of the base.

16 Claims, 9 Drawing Sheets

RAPID LOCAL ANESTHESIA LINEAR INJECTION DEVICE

CROSS-REFERENCES TO RELATED APPLICATIONS

This application is a Continuation-in-part of application Ser. No. 12/545,829 filed on Aug. 22, 2009 now U.S. Pat. No. 8,088,108.

BACKGROUND OF INVENTION

1. Field of the Invention

The present invention is directed to a Local Anesthesia Linear Injection Device; more particular to one that improves the delivery of local anesthesia.

2. Background

Current techniques for establishing local skin anesthesia involve multiple painful injections of local anesthetic into the periphery of the area to be anesthetized.

This painful procedure must unfortunately be performed very often in the outpatient setting during laceration repairs, IV insertions and other dermatologic procedures. This means that many times the already traumatized patient must undergo multiple painful injections of anesthesia over a prolonged period of several seconds to minutes. This traumatizes the patient with more than just the prolonged pain of the injections themselves, but also by the psychological trauma of seeing and feeling the needle repeatedly penetrating their skin. Many times after the pain of anesthesia infiltration there is still pain during the procedure because the clinician is not entirely sure of where the anesthesia begins and ends. This universally results in a negative patient experience, particularly in the pediatric population.

3. Prior Art

There exists prior art, U.S. Pat. No. 3,595,231 which is a device that consists in dividing a stream of the liquid to be injected into elementary streams feeding nipples connectable to injection needles. The device consists of a body, preferably constituted by a flat cylindrical disc, which comprises a main flow nipple connectable to an injection syringe, a plurality of secondary flow nipples and a network of internal ducts for dividing the main stream of the aforesaid liquid.

There is still room for improvement in the art.

SUMMARY OF THE INVENTION

This apparatus is a Local Anesthesia Linear Injection Device that is made of a very simple triangular shaped piece of clear plastic which encases multiple conduits that connect a flange on the tip of the triangle to the base of the triangle from which there are multiple tiny hypodermic needles protruding. The flange is such that a Luer Lock syringe can be attached. The number of needles would be directly proportional to the length of the device.

The device would be available in many sizes identified by the length of the base of the device. These sizes could be denoted in, but not limited to, 1 cm increments.

BRIEF DESCRIPTION OF THE DRAWINGS

Without restricting the full scope of this invention, the preferred form of this invention is illustrated in the following drawings.

BRIEF DESCRIPTION OF THE PREFERRED EMBODIMENTS

There are a number of significant design features and improvements incorporated within the invention.

The current invention is a Rapid Local Anesthesia Linear Injection Device that would significantly improve this unpleasant experience in many ways. The duration of the discomfort would be minimized to only 1-2 seconds. The psychological trauma would be limited greatly by there being no visible needle penetration. The area of anesthesia would be very well demarcated preventing painful inadvertent extension outside of the area of anesthesia. The total procedure time would be greatly reduced and the amount of user variability would be greatly controlled producing much more uniform and consistent resultant anesthesia.

As shown in FIGS. 1, 3, 4, 5 and 6, the device 1 is a very simple triangular shaped piece of clear plastic encasing multiple conduits with a flange 20 on the tip of the cone 10 where a Luer lock syringe 100 can attach.

Figure 1:
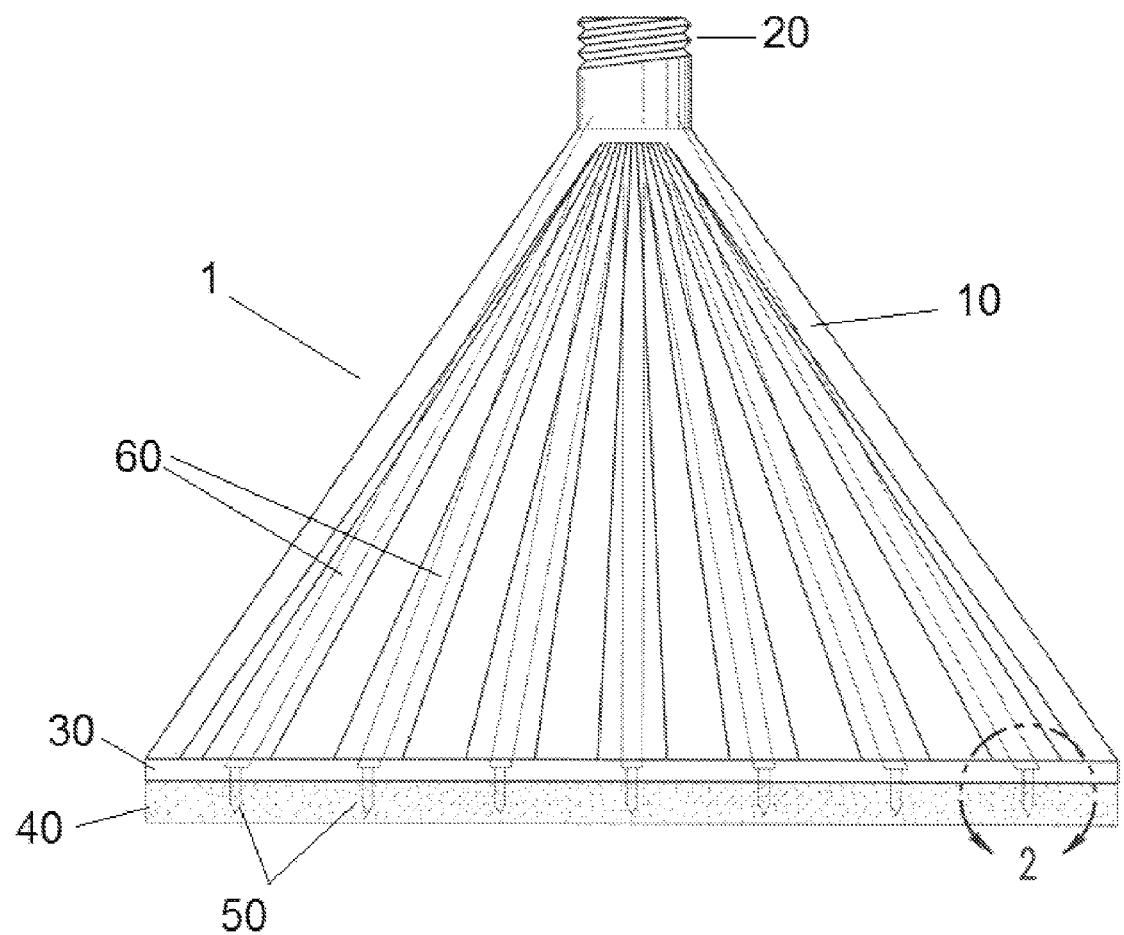
FIG. 1 is a side view of the Anesthesia Injection Strip.
Figure 2:
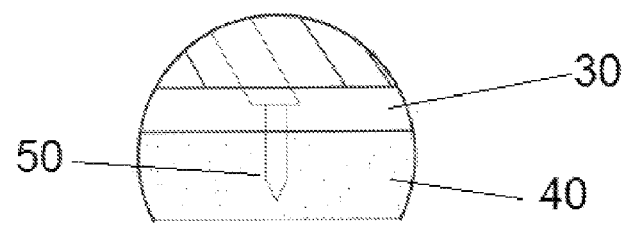
FIG. 2 is a close up of the injection point.

As shown in FIG. 2, protruding from the base 30 of the cone 10 are multiple tiny hypodermic needles 50. The number of needles 50 would be directly proportional to the length of the base of the device 1.

Figure 3:
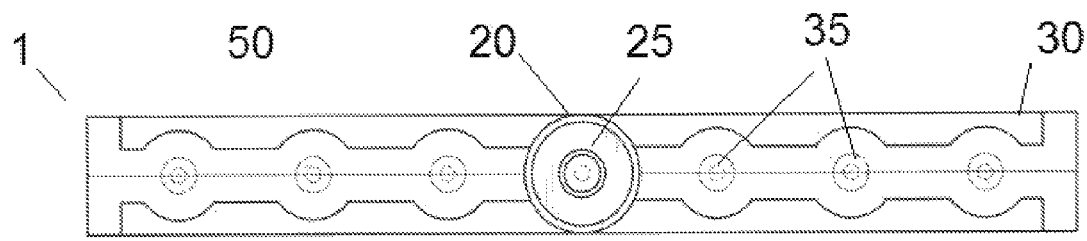
FIG. 3 is a top view of the device.
Figure 4:
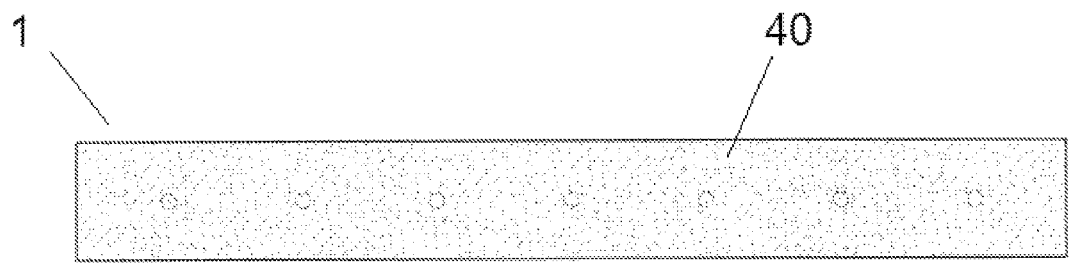
FIG. 4 is a bottom view of the device.
Figure 5:
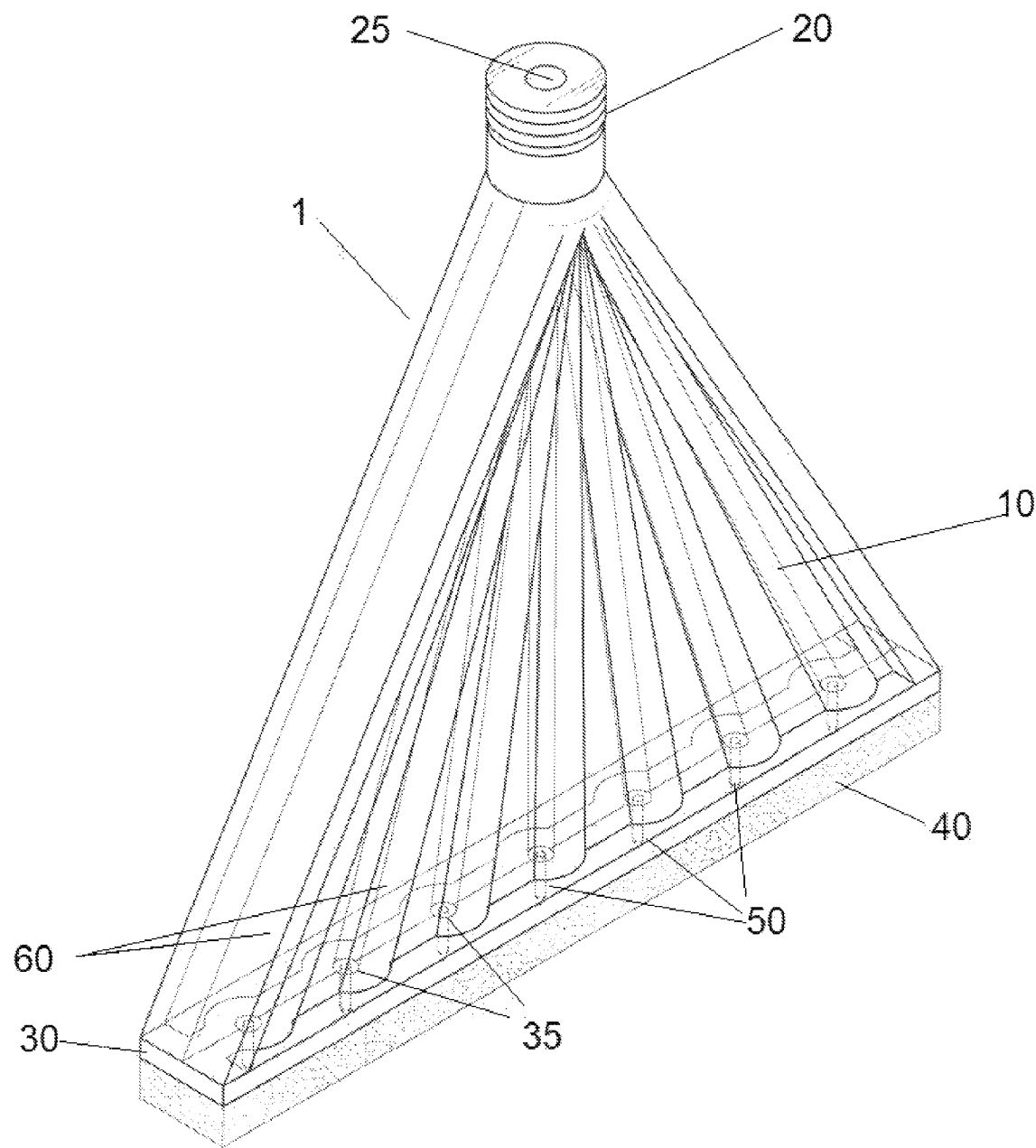
FIG. 5 is a front perspective of the device.
Figure 6:
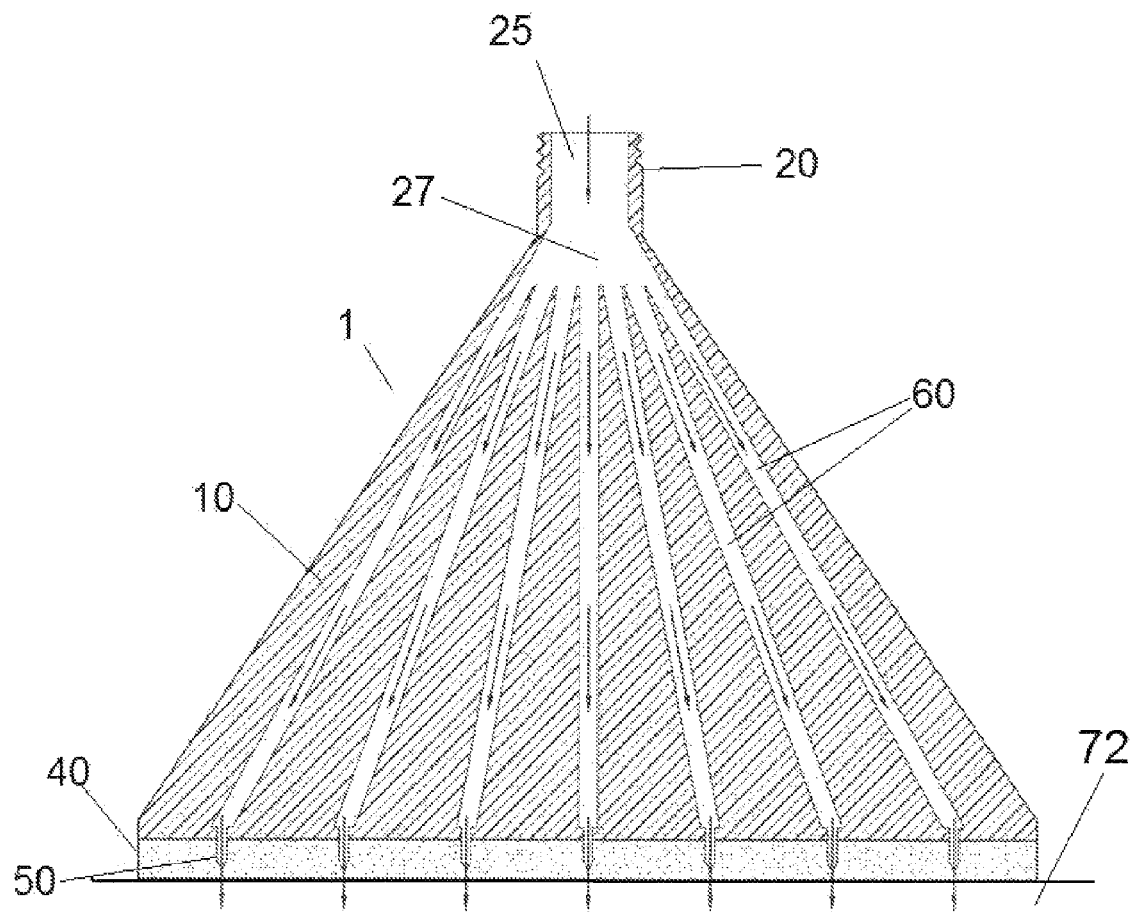
FIG. 6 is a cross-section view showing anesthesia flow.
Figure 7:
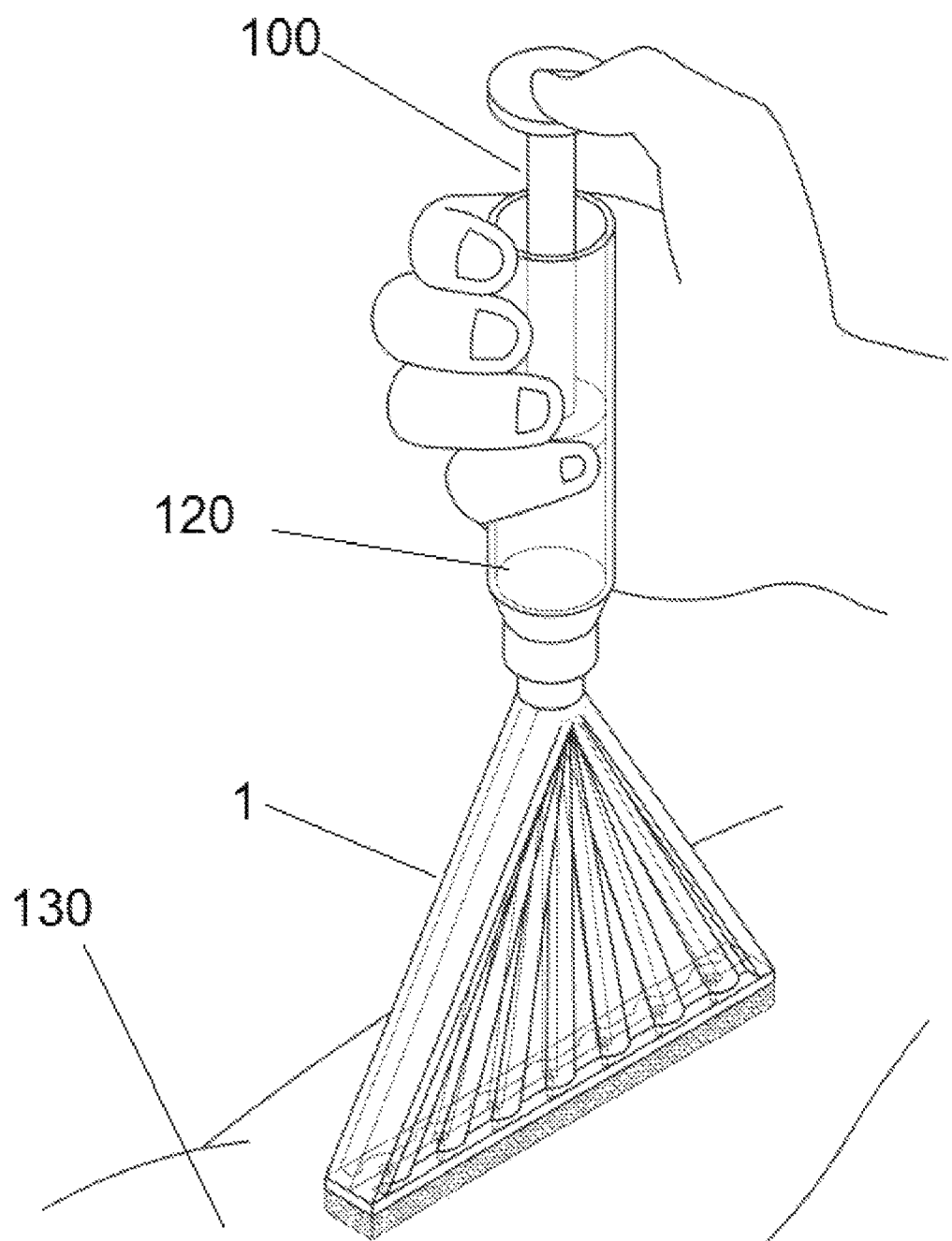
FIG. 7 displays the device being used.

As shown in FIGS. 2, 3 and 4, the device 1 is triangular in shape with a triangular body 10 with a chamber 27 at the top and a long rectangular or arc-shaped base 30 at the bottom with hypodermic needles 50 protruding from the bottom of the base 30. The outside of the top of the device has a flange 20 and an opening 25 so that an injection device such as a Luer lock syringe 100 can be attached. In one embodiment, the Luer lock syringe 100 would be loaded with the anesthesia 120 for delivery to the device 1 as shown in FIG. 7. The anesthesia 120 flows from the delivery device such as a Luer lock syringe 100 to the chamber 27 to the conduits 60 to the hypodermic needles 50 as shown in FIG. 6.

Figure 9:
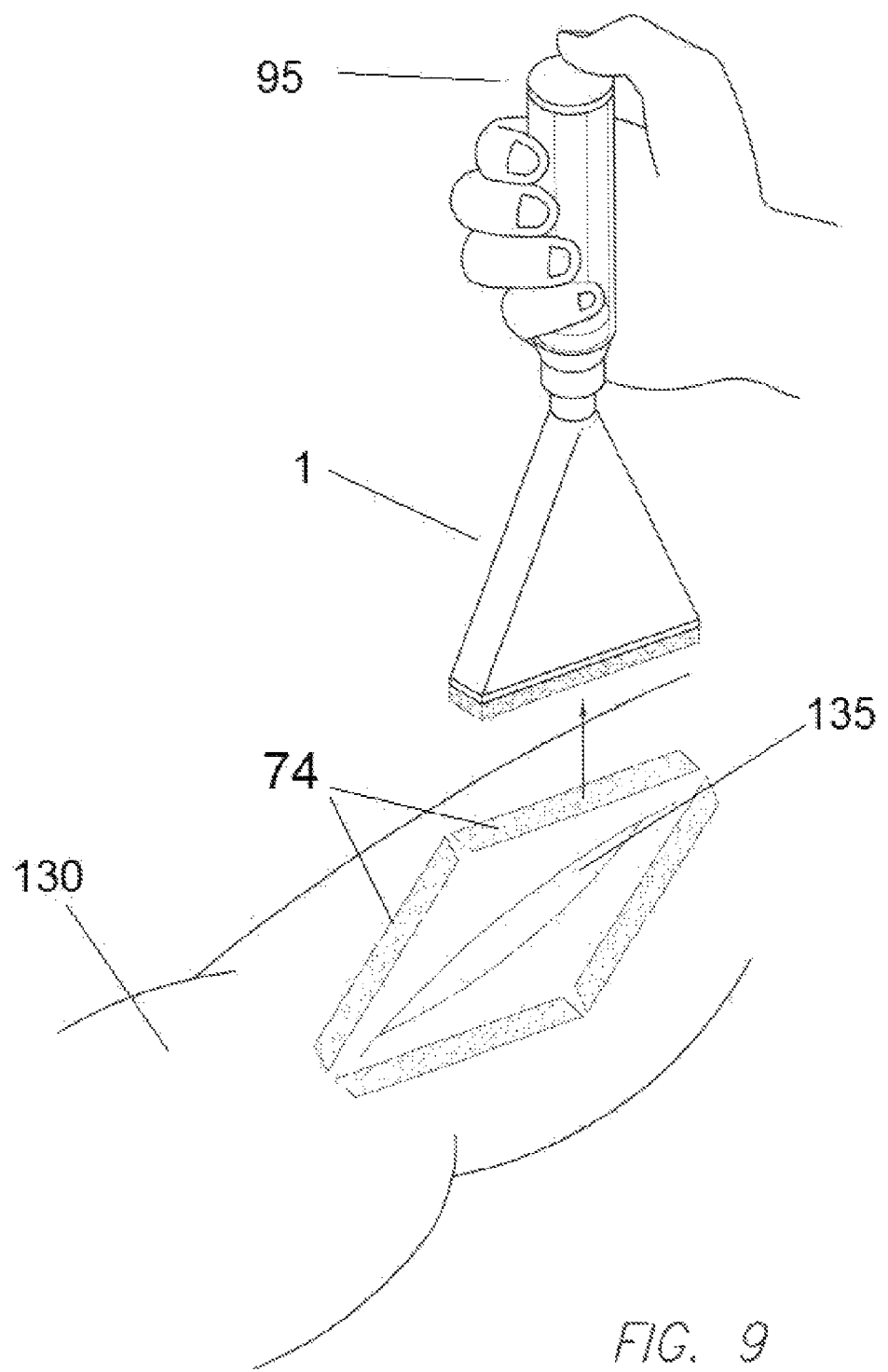
FIG. 9 displays the device with a trapezoid bottom.
Figure 10:
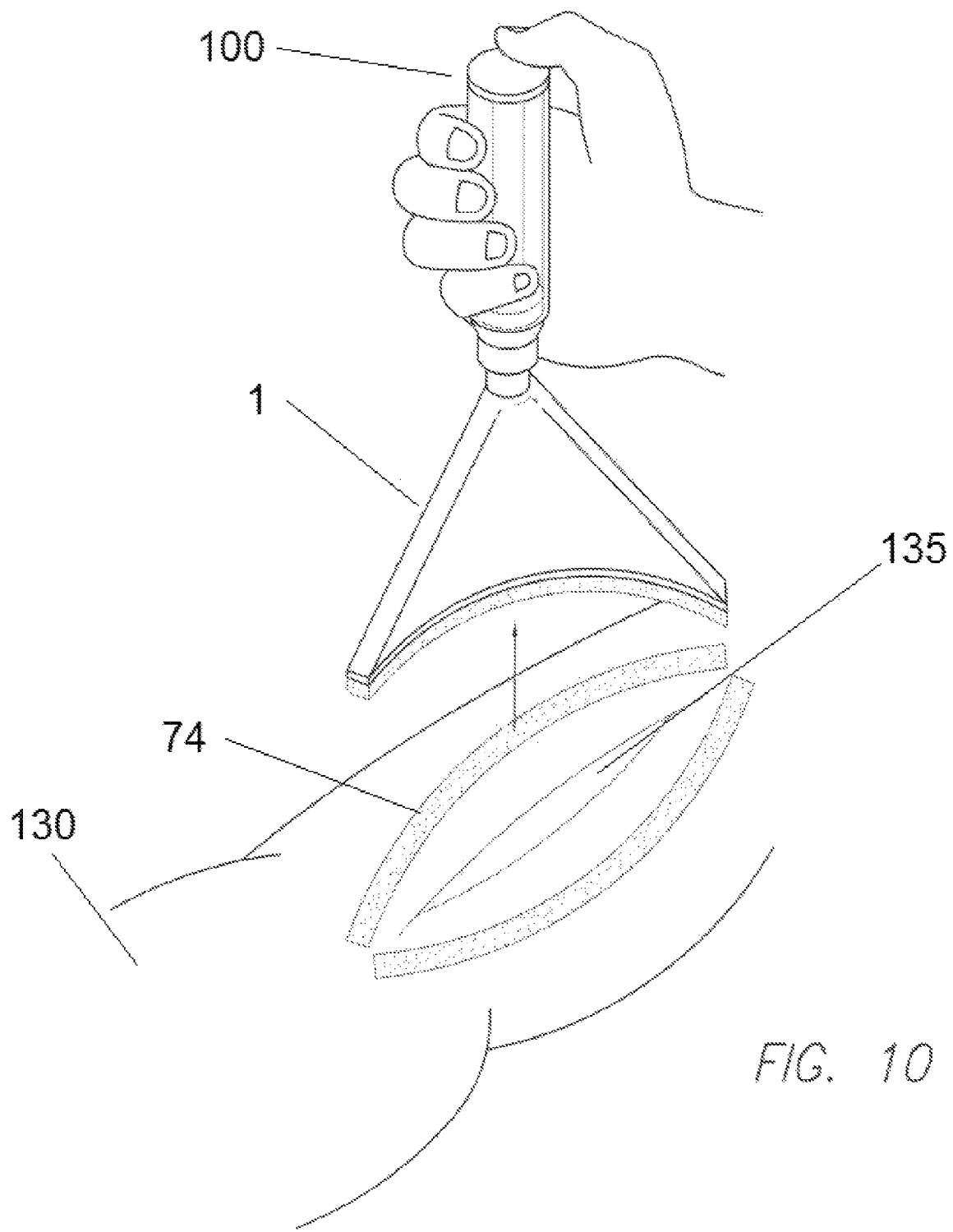
FIG. 10 displays the device with an arc shaped bottom.

The device 1 came be made in many sizes identified by the shape and the length of the base 30 of the device 10. These sizes could be denoted in, but not limited to, 1 cm increments. This would allow for significant individualization of the device determined by the size of the area that needs to be anesthetized. FIG. 9 shows the device with a trapezoid or rectangular shaped bottom and FIG. 10 shows the device with an arc shaped bottom to ease the use of the device with different types of wounds 135.

As shown in FIG. 7, the syringe 100 initially injects the anesthetic 120 into a small common chamber 27 that evenly feeds multiple conduits 60 in parallel fashion that carry equal amounts of the anesthetic to the short, very fine gauge needles which are mounted at a right angle to the base 30 of the device. The needles 50 would be distributed evenly down the base 30 of the device 10 and in the preferred embodiment spaced approximately 5 mm apart to allow for complete serial anesthesia with a minimum of anesthetic.

The needles 50 protrude from the base 30 approximately 3-5 mm and are buried in a compressible strip of rubber foam 40 which is approximately 5-8 mm thick and adherent to the base of the device. The length of the needles 50 is dependent on the compressibility factor of the foam strip 40.

Figure 8:
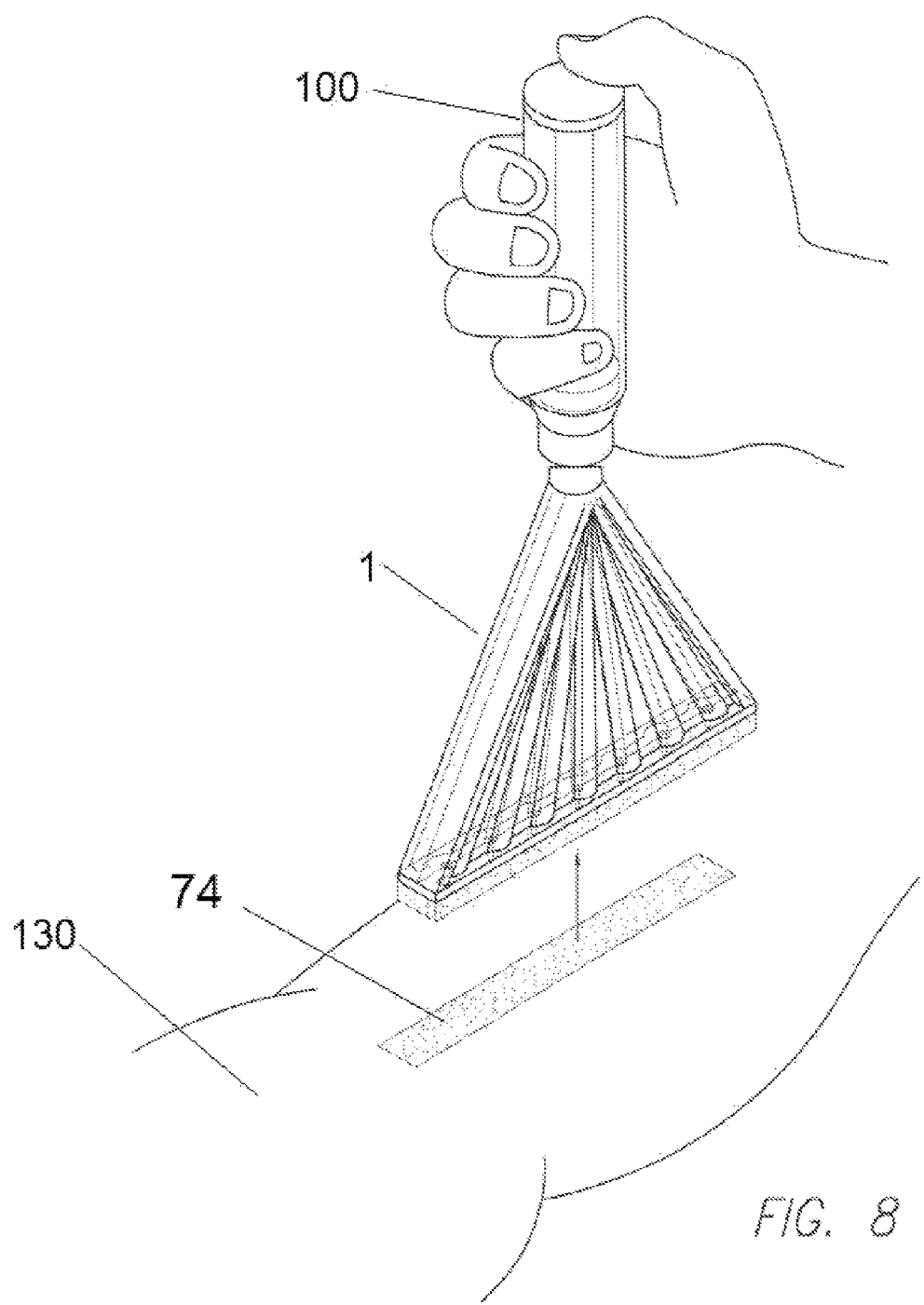
FIG. 8 displays the ink strip.

FIGS. 7 and 8 displays the device in use. The base 30 is placed against the skin 130. Force is applied down against the skin 130, exposing the hypodermic needles 50 from the foam strip 40 and allowing the hypodermic needles 50 to project into the skin 130 and the tissue underneath. The plunger of the Luer lock syringe 100 is pressed forcing the anesthesia 120 into the chamber 27 through the conduits 60 into the hypodermic needles 50 into the subcutaneous tissues 72.

In the preferred embodiment, the foam strip 40 also has a small amount of skin marking dye 70 in it to leave a temporary stripe 74 stamped on the skin, demarcating the area of anesthesia as shown in FIG. 8. This stamp is used to identify exactly where the anesthesia 120 has been applied and could be color-coded to identify the type of anesthetic used 120. This color-coding would allow health professionals to make sure that a patient is properly dosed.

Figure 11:
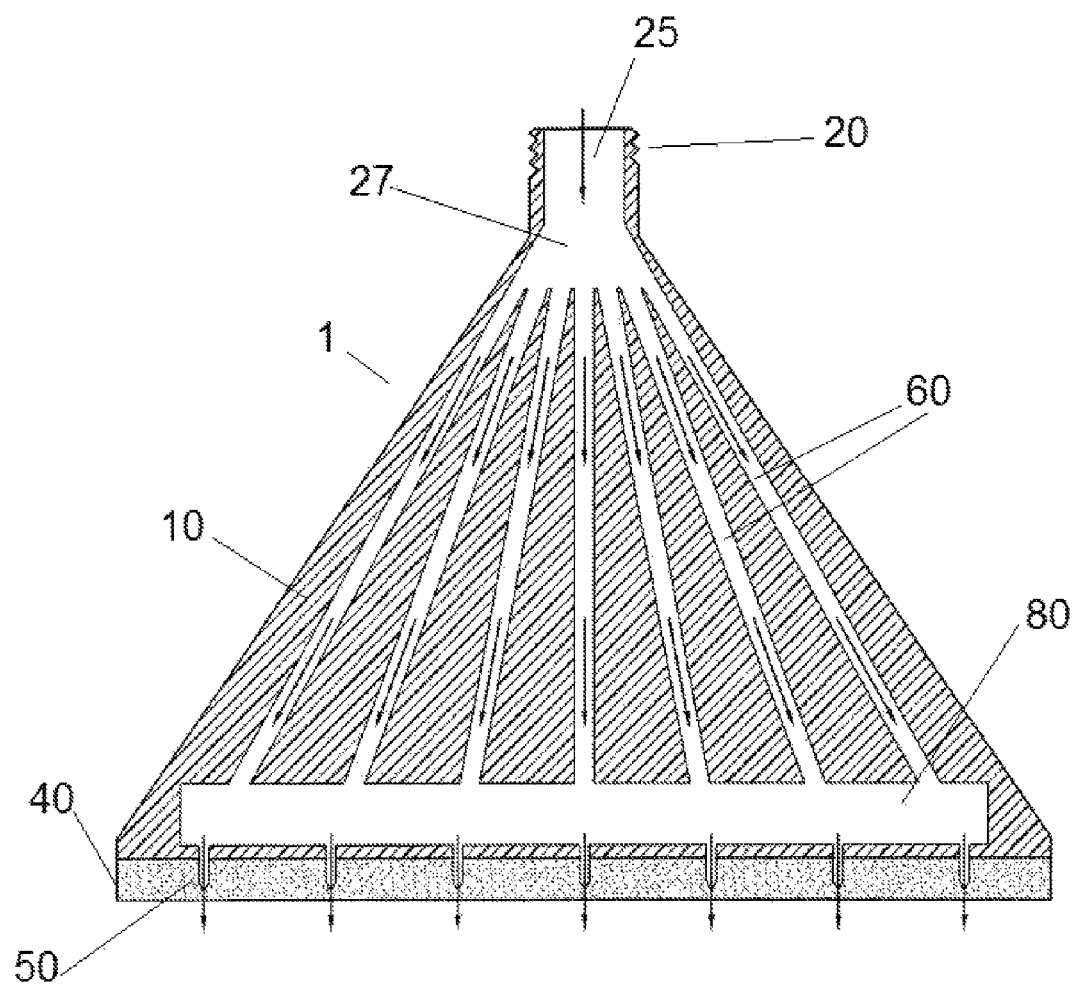
FIG. 11 is a cross-section view showing anesthesia flow in the embodiment with a common chamber.

In one embodiment, the conduits 60 are matched to the number of injection needles 50. In an alternative embodiment there is a lesser number of conduits 60 than injection needles 50 where the conduits feed to a common chamber 80 contiguous with the injection needles as shown in FIG. 11. Each embodiment would assure equal amounts of anesthetic fed to each needle 50.

Although this device is demonstrated here primarily as something intended to be attached to a Luer-Lock syringe 100, this does not exclude the potential to be utilized as part of a device that has a self-contained sealed ampule 95 of anesthetic 120 thus requiring no additional syringe or supplies. In this alternative embodiment, the one-time-use device 1 with the self-contained sealed ampule 95 of anesthetic 120 would be even more time efficient and allow for even greater ease of use for emergent surgical procedures.

The device could also be used to inject other drugs and liquids such as medical doses other then anesthesia. The skin marking dye 70 can be color or pattern coded to identify what was injected.

As to a further discussion of the manner of usage and operation of the present invention, the same should be apparent from the above description. Accordingly, no further discussion relating to the manner of usage and operation will be provided.

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A device for the injection of local anesthesia comprising: a triangular-shaped plastic device with a base on one end and a chamber and a flange on an opposite end, with a plurality of conduits that run from the chamber to a plurality of needles that extend out from the base with the needles having a length from 3 to 5 millimeters, having a delivery device connected to the flange and having a foam strip attached to the base covering the needles.

2. A device according to claim 1 further comprising having the base in a long rectangular shape.

3. A device according to claim 1 further comprising having the base in an arc shape with a flat, planar bottom.

4. A device according to claim 1 further comprising having the delivery device be a Luer-lock syringe.

5. A device according to claim 1 further comprising having the delivery device being self-contained means attached to the chamber.

6. A device according to claim 5 further comprising having the self-contained means as an ampule.

7. A device according to claim 1 further comprising having the foam strip contain a skin-marking dye.

8. A device according to claim 7 further comprising having the skin-marking dye be color-coded to identify the injection.

9. A device for local anesthesia injection comprising: a triangle-shaped device with a base on one end and a chamber and a flange on an opposite end, with a plurality of conduits that run from the chamber to a common chamber in the base which is connected to a plurality of needles that extend out from the base with the needles having a length from 3 to 5 millimeters, having a delivery device connected to the flange and having a foam strip attached to the base covering the needles.

10. A device according to claim 9 further comprising having the base in a long rectangular shape.

11. A device according to claim 9 further comprising having the base in an arc shape with a flat, planar bottom.

12. A device according to claim 9 further comprising having the delivery device be a Luer-lock syringe.

13. A device according to claim 9 further comprising having the delivery device being self-contained means attached to the chamber.

14. A device according to claim 13 further comprising having the self-contained means as an ampule.

15. A device according to claim 9 further comprising having the foam strip containing a skin-marking dye.

16. A device according to claim 15 further comprising having the skin-marking dye color-coded to identify the injection.

* * * * *